(12) United States Patent  
Gall

(10) Patent No.: US 6,713,498 B2
(45) Date of Patent: Mar. 30, 2004

(54) METHOD FOR TREATING GLAUCOMA VI

(75) Inventor: Martin Gall, Morristown, NJ (US)

(73) Assignee: Alteon Incorporated, Ramsey, NJ (US)

( * ) Notice: Subject to any disclaimer, the term of this patent is extended or adjusted under 35 U.S.C. 154(b) by 73 days.

(21) Appl. No.: 10/158,685

(22) Filed: May 30, 2002

(65) Prior Publication Data

US 2003/0004195 A1 Jan. 2, 2003

Related U.S. Application Data

(60) Provisional application No. 60/294,409, filed on May 30, 2001.
(51) Int. Cl.[7] ................... C07D 407/06; C07D 413/08; C07D 417/06; A61K 31/4178
(52) U.S. Cl. ................ 514/361; 514/363; 514/364; 514/365; 514/383; 514/347; 548/128; 548/138; 548/143; 548/203; 548/204; 548/266.4; 548/311.4
(58) Field of Search ................. 514/361, 363, 514/364, 365, 383, 347; 548/128, 136, 143, 203, 204, 266.4, 311.4

(56) References Cited

U.S. PATENT DOCUMENTS 5,889,032 A * 3/1999 Lohray et al. .............. 514/369

* cited by examiner

*Primary Examiner*—Robert Gerstl
(74) *Attorney, Agent, or Firm*—Mintz, Levin, Cohn, Ferris, Glovsky and Popeo, P.C.; Ivor R. Elrifi

(57) ABSTRACT

Provided, among things, is a method of decreasing intraocular pressure in an animal, including a human, comprising administering an intraocular pressure decreasing amount of a compound of the formula I:

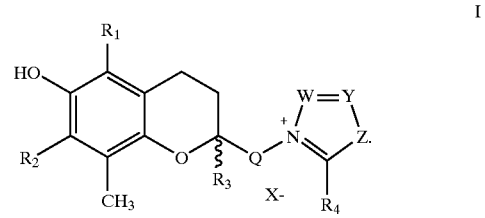

24 Claims, No Drawings

METHOD FOR TREATING GLAUCOMA VI

This application claims the priority of U.S. application Ser. No. 60/294,409, filed May 30, 2001.

The present invention relates to methods for treating glaucoma or improving accommodation (i.e. the process by which the eye adjusts for vision at different distances). In one aspect, the present invention relates to a method of decreasing the intraocular pressure caused by glaucoma.

Diabetes is the major determinant to the development of visual disability and blindness in parts of the world unencumbered by causes related to malnutrition or infectious diseases. Retinopathy is the leading cause of blindness in diabetics and is a progressive, degenerative disease. Of the many risk factors believed to be associated with diabetic retinopathy, the level of glucose in the plasma has been widely investigated. It is well accepted that a lower incidence of retinopathy is associated with decreased plasma levels of glucose.

Ophthalmologic disorders in diabetes include opacification and glaucoma. The occurrence of these indications is correlated with the persistent hyperglycemia of the disease. Although the incidence of glaucoma is significant in diabetic populations, glaucoma affects a substantial portion of the general aging population as well.

Primary open angle glaucoma occurs in approximately 4% of diabetics compared to 1.8% of the general population. The reasons for the increase in intraocular pressure that is observed in this disorder are not completely understood. The increase in intraocular pressure that characterizes glaucoma is likely caused by an impairment in the drainage of fluid from the eye at the trabecular meshwork since trabeculectomy restores, at least for a period of time, normal intraocular pressures. The origin of this impairment to fluid movement is currently unknown but may be related to a physical obstruction or restriction to movement of proteins that make up a sieving system in the trabecular meshwork. The trabecular meshwork functions as a sieving system that maintains a restricted flow of intraocular fluid from the eye. The result of excess restriction of this flow is a back pressure that causes increased intraocular pressure.

Replacement of the trabecular meshwork (trabeculectomy) remains an established surgical procedure for improving the filtering of intraocular fluid and for overall reduction of intraocular pressure. This remedy is invasive and of limited effectiveness, since pressure elevation frequently recurs after the procedures.

Current chronic pharmaceutical therapies impose a measure of risk on an already medically compromised patient population. The use of topical B-blockers may affect underlying cardiovascular disease, and carbonic anhydrase inhibitors (e.g. Diamox™) may cause metabolic acidosis. The use of pressure-lowering drugs will be affected by the state of renal disease in compromised elderly and diabetic patients. The drawbacks associated with current pharmaceutical therapies highlight an unmet medical need for a chronic pharmaceutical intervention that is distinct in mechanism of action from current therapies.

New strategies for pharmaceutical intervention in the treatment of glaucoma based upon new mechanisms of action need to be identified. In addition, pharmaceutical agents that decrease the intraocular pressure associated with glaucoma are needed. Also, the methods of improving accommodation provided by the invention allow one to avoid costly and burdensome optical solutions, such as the use of separate reading glasses or glasses with bifocal lenses.

SUMMARY OF THE INVENTION

In one embodiment, the invention relates to a method of treating or ameliorating or preventing glaucoma, decreasing intraocular pressure or improving or ameliorating ocular accommodation in an animal, including a human, comprising administering an intraocular pressure decreasing or ocular accommodation improving amount of a compound of the formula I:

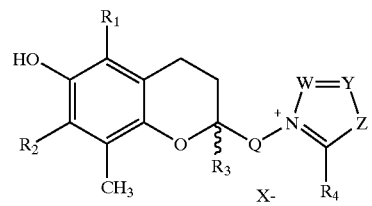

wherein: W and Y are independently N or, respectively, $CR^W$ or $CR^Y$. Z is O, S or $NR^Z$. Q is —$CH_2$— or —(CO)—$CH_2$—, where the methylene is bonded to a ring nitrogen. $R^W$ and $R^Y$ are independently hydrogen, alkyl, —C≡$CR^E$, —$CH_2$—C≡$CR^P$, alkenyl, aryl, arylalkyl, aryloxy, arylthio, amino, alkylamino, arylamino, dialkylamino, diarylamino, $CH_3C(O)NH$—, fluoroalkyl, perfluoroaryl, hydroxyalkyl, $C(O)NH_2$, and $S(O)_2NH_2$ or, together with their ring carbon atoms form a fused 6-membered aromatic or heteroaromatic ring, wherein $R^E$ or $R^P$ is alkyl, hydrogen, hydroxyalkyl or aryl. $R^Z$ is alkyl, —$CH_2$—C≡$CR^P$, aryl, arylalkyl, or aroylalkyl. $R^1$ and $R^2$ are independently hydrogen, alkyl or hydroxymethyl. $R^3$ is hydrogen or methyl. $R^4$ is acetamido, hydrogen, methyl, amino, —C≡$CR^E$, —$CH_2$—C≡$CR^P$ alkylthio, fluoromethyl, difluoromethyl, trifluoromethyl, cyanomethyl, hydroxyalkyl, alkoxycarbonyl-methyl, 1-(alkoxycarbonyl)-1-hydroxyalkyl or aminocarbonylmethyl. (The "1" notations of "1-(alkoxycarbonyl)-1-hydroxyalkyl" indicates that a terminal methyl [but for the recited substitutions] of "alkyl" is substituted with the hydroxyl and esterified carbonyl.)

DETAILED DESCRIPTION OF THE INVENTION

In accordance with the present invention a method is provided for the treatment of an animal, preferably a mammal, preferably a human with ophthalmologic disorders including glaucoma and reduced accommodation. Briefly the method of the present invention provides for a method of treatment of mammals with glaucoma or reduced accommodation that can be caused by age or certain age-related diseased states such as diabetes. The method provides for administration of classes of inhibitors of advanced glycation. The invention further provides for methods to monitor the improvement in the ocular condition during the course of the administration of compound.

Primary open angle glaucoma is characterized by an increase in intraocular pressure. The condition of open angle glaucoma is characterized by an increase in the pressure within a person's eye or eyes, called the intraocular pressure. The normal pressure is about 15 mmHg. Elevated pressures of 20–30 mm Hg create a strong risk of damage to the optic nerve and blindness.

Glucose reacts with proteins by a non-enzymatic, post-translational modification process called non-enzymatic glycosylation. The resulting sugar-derived adduct, the advanced glycosylation end product (AGE), matures to a molecular species that is reactive, and can readily bond to amino groups on adjacent proteins, resulting in the formation of AGE cross-links between proteins.

It has now been found that certain compounds that inhibit the formation of such sugar-derived adducts, or in some cases are believed to deactivate such adducts or break resulting crosslinks, can reduce intraocular pressure or ameliorate a trend towards elevated pressure.

Structural matrix proteins isolated from tissues of diabetics and aged individuals are more highly crosslinked than those from nondiabetics or younger individuals and are more resistant to both enzymatic and chemical hydrolysis in vitro. It is this cross-linked state of proteins that is believed to cause stiffness of tissues. The cleavage of AGE cross-links between proteins can provide a mechanism-based therapy for restoration of normal tissue function. An agent that cleaves AGE cross-links between proteins or inhibits their formation can restore more normal sieving function and movement to the trabecular meshwork.

In accordance with the present invention, methods for administering pharmaceutical compositions containing cross-link breaking agents or agents which inhibit the formation of AGE cross-linked structures have been developed for treating glaucoma, intraocular pressure associated with glaucoma and reduced accommodation. These agents are derived from heteroaromatic 5-membered or fused bicyclic rings, as shown in Scheme 1 below:

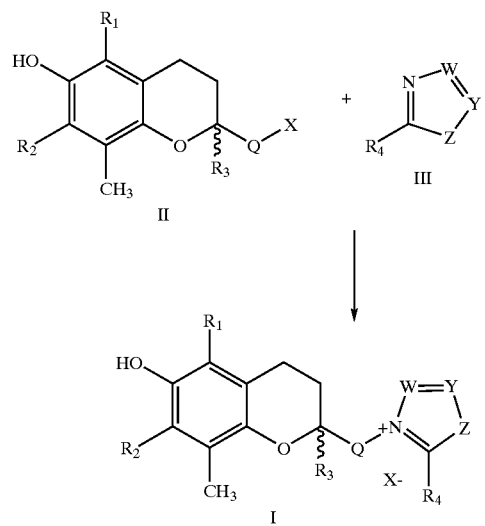

Scheme 1

Preferred compounds of the present invention include compounds derived from the heterocycles defined by III, including, but not limited to, oxazoles, thiazoles, imidazoles, [1,3,4]- and [1,2,4]-oxadiazoles, [1,3,4]- and [1,2,4]-thiadiazoles, [1,2,4]-triazoles, benzoxazoles, and benzothiazoles and the like, by their treatment with the 6-chromane derivative II, neat, or in a suitable polar solvent, such as acetonitrile, dimethylformamide, N-methyl-pyrrolidone, dimethylsulfoxide, methanol or ethanol, or aqueous mixtures of these organic solvents, at from room temperature to 60° C. for from 1 to 96 hours. (See Scheme 1.).

It is recognized by those skilled in the art that pyrazoles, indazoles, benzothiazoles, benzoisothiazoles, isothiazoles, isoxazoles, benzisoxazoles, [1,2,3]-triazoles, [1,2,3]-oxadiazoles and [1,2,3]-thiadiazoles may be treated with II to prepare analogous azolium salts, which are not explicitly described by structure I in Scheme 1.

It is further recognized by those skilled in the art that when either W or Y=N (Scheme 1, structure III), alkylation of III may also occur on that nitrogen, in addition to the alkylation on the nitrogen atom shown in product I, to yield mixtures of product. In this situation, the addition of one equivalent or less of a suitable acid, such as the appropriate volume of an ethereal HCl or ethereal HBr solution prior to the addition of III, will alter the ratio of the isomers formed. Where isomeric addition products are formed, they may be separated by chromatographic methods such as HPLC or, more preferably, by selective crystallization.

It will also be recognized by those skilled in the art that the carbon of the chromane structure bearing the group Q is asymmetric and can exist in one of two configurations, (R) or (S). When equal mixtures of (R) and (S) forms are present, the compound exists as a non-optically active racemic mixture. The present invention covers the racemates and each single, optically pure or enriched enantiomeric derivative. It will further be recognized that the tools for isolating enantiomers with chiral specific chromatographic methods and crystallographic methods (typically using chiral salts) have developed to make such isolations generally applicable.

The alkyl, and alkenyl groups referred to below include both $C_1$ to $C_6$ linear and branched alkyl and alkenyl groups, unless otherwise noted. In addition, alkoxy groups include linear or branched $C_1$ to $C_6$ alkoxy groups, unless otherwise noted. Alkyl' represents a second alkyl group independently selected from the same $C_1$ to $C_6$ linear or branched selection.

Consistent with the rules of aromaticity, Ar, or aryl, refers to a $C_6$ or $C_{10}$ aromatic ring, optionally substituted as set forth below, or a 5- or 6-membered heteroaromatic (heteroaryl) ring containing at least one and up to three atoms of N for the 6-membered heteroaryl ring and from one to three atoms of N or one atom of O or S and zero to two atoms of N for the 5-membered heteroaryl ring; each heteroaromatic ring can be substituted with up to two amino-, dialkylamino-, pyrrolidin-1-yl, piperidin-1-yl, morpholin-4-yl, thiamorpholin-4-yl, 4-(aryl)piperidin-1-yl, 4-(aryl)piperazin-1-yl-(said aryl group optionally substituted as described below), halo (particularly fluoro) or alkylenedioxy groups, or fused to a substituted benzene, pyridine, pyrimidine, pyridazine or triazine ring, and wherein $C_6$ or $C_{10}$ aromatic and heteroaromatic rings can be additionally substituted as set forth below.

$C_6$ or $C_{10}$ aromatic rings can be additionally substituted with acylamino, acyloxyalkyl, alkanoyl, alkanoylalkyl, alkenyl, alkoxy, alkoxycarbonyl, alkoxycarbonylalkyl, alkyl, alkylamino, ($C_1$–$C_3$)-alkylenedioxy, alkylsulfonyl, alkylthio, allyl, amino, benzoyl, carboxy, carboxyalkyl, cyano, cycloalkyl, dialkylamino, halo, fluoromethyl, difluoromethyl, trifluoromethyl, hydroxy, ($C_1$–$C_6$)-hydroxyalkyl, mercapto, nitro, phenoxy, phenyl, phenylalkyl, sulfamoyl, sulfo (—$SO_3H$), aminosulfonyl ($H_2NSO_2$—), phenylsulfonyl, or phenylsulfinyl.

Heteroaromatic rings can be additionally substituted with acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, cyano, dialkylamino, halo, fluoralkyl, hydroxy, mercapto, nitro, phenyl, phenoxy, pyrrolidin-1-yl, piperidin-1-yl, 4-arylpiperidin-1-yl, morpholin-4-yl, 4-arylpiperazin-1-yl, sulfamoyl, fluoromethyl, difluoromethyl, or trifluoromethyl.

The halo atoms can be fluoro, chloro, bromo or iodo. $X^-$ is a pharmaceutically acceptable anion.

The compounds of formula I comprise biologically and pharmaceutically acceptable salts. Useful salt forms include the halides, particularly bromide and chloride, brosylate, tosylate, methanesulfonate (mesylate), and mesitylene-sulfonate salts. It is recognized that appropriate acetate, fumarate, maleate and succinate derivatives may be prepared from the chloride salt via ion exchange techniques. Other related salts can be formed using similarly non-toxic, and biologically and pharmaceutically acceptable anions.

Compounds of the formula II can be conveniently prepared by chemical methods well known in the art. The known acid IV (trolox; see Scheme 2), or its phenol protected derivatives IVa, IVb and IVc may be treated with lithium hydride at 0° C. in a dry, ethereal solvent for one hour, followed by treatment with methyl lithium in ether at the same temperature. The deprotected methyl ketone isolated after acidification and purification may then be treated with bromine to generate II (X=Br). Alternatively, IV may be treated with thionyl chloride, the acid chloride isolated and treated with diazomethane followed by HCl and deprotection to afford the corresponding chloroketone, II (X=Cl).

stituted acyclic precursors that are well known in the art. Non-limiting examples of such syntheses are described below.

The pyrazole compounds of the invention can be prepared by reaction of hydrazine derivatives with 1,3-dicarbonyl compound (Scheme 3). For example, 1,3-diketones having aryl substituents can be used to prepare 3-arylpyrazole (i.e. Y=Ar) compounds. As will be recognized by those in the art, use of unsymmetrically substituted 1,3-dicarbonyl compounds with alkyl or aryl hydrazines often lead to isomeric mixtures of pyrazole products. These isomeric mixtures can be separated by well-known separation techniques such as fractional crystallization, column chromatography, and the like.

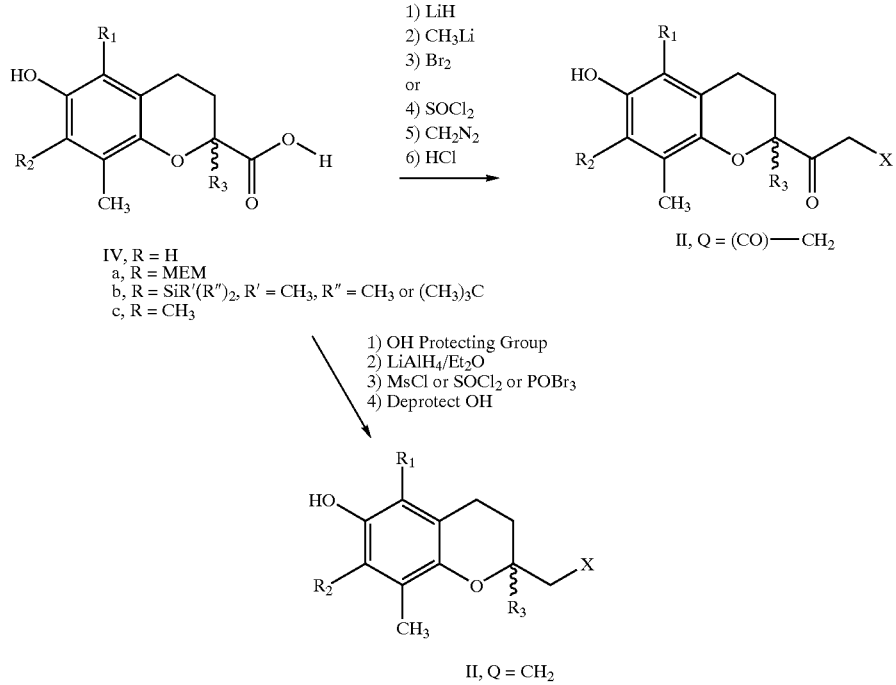

As is recognized many of the nitrogen containing heterocycles of the invention (compounds of formula III) are commercially available from chemical supply houses or are readily synthesized by methods well known in the art. For instance, certain substitution patterns can be obtained by electrophilic and nucleophilic substitution reactions on the heterocycle and are well known in the art. In addition selected nitrogen heterocycles are susceptible to metalation with organoalkali reagents, for example, n-butyllithium. The intermediate metalated-heterocycles can be treated with electrophiles, such as methyl iodide, formaldehyde, acetaldehyde, acetone, methyl pyruvate and others, to provide additional routes to specifically substituted aromatic nitrogen heterocycles.

Certain aromatic nitrogen containing heterocycles can be obtained by cyclization and cycloaddition reactions of sub-

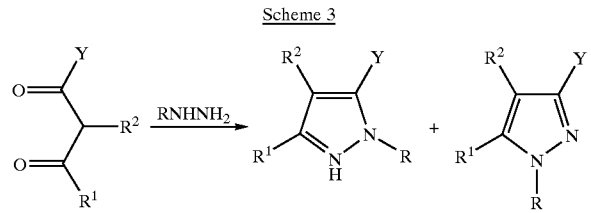

3-Aminopyrazole compounds (Y=NH$_2$) of the invention can be prepared by reaction of aryl hydrazones with ketones and aldehyde containing an α-nitrile moiety (Scheme 4, Bouveault, M. L. *Bull. Soc. Chim. Fr.,* 1890, 4, 647). 3-Aminopyrazoles can also serve as intermediates for 3-acylamino-, 3-ureido-, and 3-thioureidopyrazoles of the invention.

For example, 3-aminopyrazoles can be heated with esters to form 3-acylaminopyrazoles of the invention. The 3-aminopyrazoles are heated with formic acid to provide 3-formylaminopyrazoles. Likewise, treatment of 3-aminopyrazoles with isocyanates and isothiocyanates lead to the 3-ureido and 3-thioureido compounds (respectively) of the invention.

3- and 5-Aryl and alkyl isoxazoles of the invention are prepared by use of the chloro substituted α,β-unsaturated ketones with hydroxylamine (Scheme 7). The isomeric products can be isolated by separation techniques such as fractional crystallization, distillation, or column chromatography. Alternatively, 5-aryl substituted isoxazoles can be prepared from acetophenones (Scheme 7, Lin, Y. Lang, S. A. *J. Heterocyclic Chem.*, 1977, 14, 355).

Scheme 4

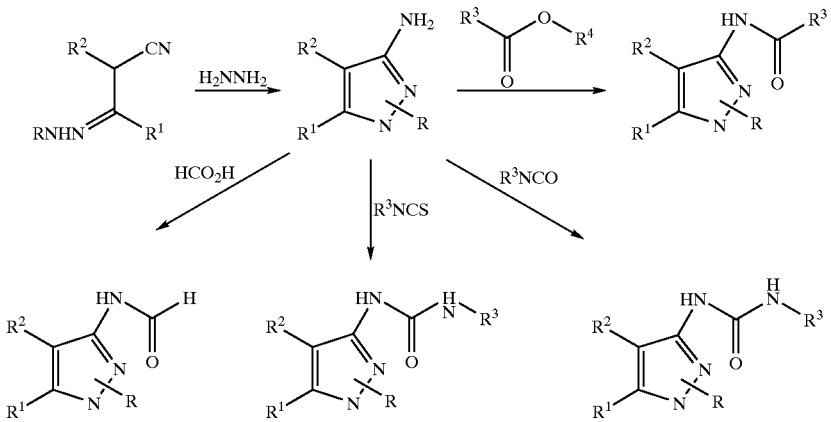

Indazoles of the invention substituted with alkyl and aryl substituents at the 3-position are synthesized from benzene analogs containing ortho-halo ketones and aldehydes (Scheme 5). For example, an indazole containing a 3-phenyl substituent can be prepared from a benzophenone analog containing a bromo moiety ortho to the carbonyl.

Scheme 5

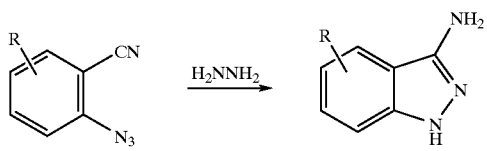

3-aminoindazoles are similarly prepared from substituted benzene precursors. A 2-azidobenzonitrile can be treated with hydrazine to prepared 3-aminoindazoles of the invention (Scheme 6, Paterson, T. M.; Smalley, R. K.; Sushizky *Tetrahedron Lett.*, 1977, 3973). 3-Acylamino-, 3-ureido-, and 3-thioureidoindazoles of the invention can be prepared from the 3-aminoindazoles using esters, isocyanates, and isothiocyanates (as described above using 3-aminopyrazoles).

Scheme 6

Scheme 7

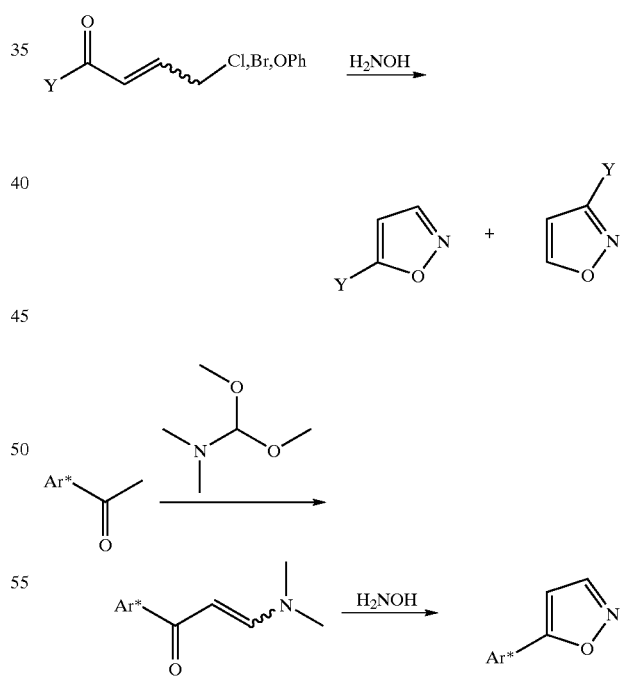

5-Aminoisoxazoles of the invention can be prepared from α-halo substituted oximes by reaction with sodium cyanide (Scheme 8, Lozanovic, M. et al. *Chem. Abstr.*, 1981, 94, 192202c). The 5-amino group can be reacted with the reagents described above for 3-aminopyrazoles to provide acylamino-, ureido-, and thioureido isoxazoles of the invention.

Scheme 8

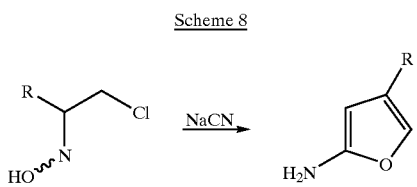

Alkyl and aryl substituted isothiazoles of the invention are prepared by the cyclization of β-imino thionocarbonyl compounds (Scheme 9). Oxidizing reagents well known in the art such as peroxides, chloranil, iodine, and the like, promote the cyclization. For example, starting material with an aryl thionocarbonyl group β-substituted to an imino group can be used to prepare a 5-aryl substituted isothiazole.

Scheme 9

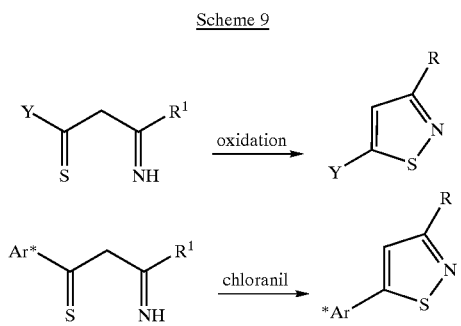

5-Amino isothiazoles of the invention can be prepared similarly (Scheme 10). Enamines can be treated with isothiocyanates to yield thioamide intermediates. The thioamides can be cyclized using oxidizing agents to provide 5-aminoisothiazoles of the invention. The 5-amino group can be reacted with the reagents described above for the 3-aminopyrazoles to provide acylamino-, formylamino-, ureido-, and thioureido-isoxazoles of the invention.

Scheme 10

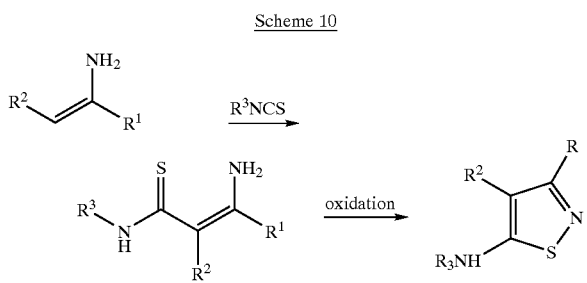

Aryl and alkyl 1,2,4-triazoles of the invention are prepared from acyl amidrazones as shown in Scheme 11. Amino-substituted 1,2,4-triazoles are formed analogously from acylaminoguanidine precursors.

Scheme 11

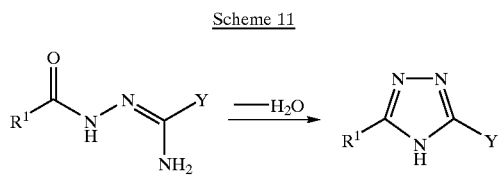

Y=Ar*, alkyl, —NH$_2$, NHAr*, NHalkyl

To treat glaucoma or reduced accommodation and its associated symptoms, an effective amount of a pharmaceutical compound will be recognized by clinicians and includes an amount effective to reduce, ameliorate or eliminate one or more symptoms of the disease sought to be treated or the condition sought to be avoided or treated, or to otherwise produce a clinically recognizable change in the pathology of the disease or condition.

In treating glaucoma, agents of the invention can be administered concurrently or in a combined formulation with one or more $\alpha_2$-selective adrenergic agonists, carbonic anhydrase inhibitors or prostaglandin analogs. Examples of $\alpha_2$-selective adrenergic agonists include clonidine, apraclonidine, guanfacine and guanabenz, which are administered in effective amounts as is known in the art. Examples of carbonic anhydrase inhibitors include acetazolamide, dichlorphenamide and methazolamide, which are administered in effective amounts as is known in the art. Examples of prostaglandin analogs include PGE$_2$ and PGF$_{2\alpha}$. analogs, which are administered in effective amounts as is known in the art, including effective amounts administered by topical application to the eye. Thus, the invention further provides pharmaceutical compositions comprising an agent of the invention in combination with an effective amount of an $\alpha_2$-selective adrenergic agonist, carbonic anhydrase inhibitor, prostaglandin analog, or combination thereof.

Pharmaceutical compositions can be prepared to allow a therapeutically effective quantity of the compound of the present invention, and can include a pharmaceutically acceptable carrier, selected from known materials utilized for this purpose. See, e.g., Remington, The Science and Practice of Pharmacy, 1995; Handbook of Pharmaceutical Excipients, 3$^{rd}$ Edition, 1999. Such compositions can be prepared in a variety of forms, depending on the method of administration.

In addition to the subject compound, the compositions of this invention can contain a pharmaceutically acceptable carrier. The term "pharmaceutically acceptable carrier", as used herein, means one or more compatible solid or liquid filler diluents or encapsulating substances that are suitable for administration to an animal, including a mammal or human. The term "compatible", as used herein, means that the components of the composition are capable of being commingled with the subject compound, and with each other, such that there is no interaction that would substantially reduce the pharmaceutical efficacy of the composition under ordinary use situations. Preferably when liquid dose forms are used, the compounds of the invention are soluble in the components of the composition. Pharmaceutically-acceptable carriers must, of course, be of sufficiently high purity and sufficiently low toxicity to render them suitable for administration to the animal (including human) being treated.

Examples of substances which can serve as pharmaceutically-acceptable carriers or components thereof include: sugars, such as lactose, glucose and sucrose; starches, such as corn starch and-potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the subject compound is basically determined by the way the compound is to be administered. If the subject compound is to be injected, the preferred pharmaceutically-acceptable carrier is sterile, physiological saline, with a blood-compatible suspending agent, the pH of which has been adjusted to about 7.4.

If the preferred mode of administering the subject compound is perorally, the preferred unit dosage form is therefore tablets, capsules, lozenges, chewable tablets, and the like. Such unit dosage forms comprise a safe and effective amount of the subject compound, which is preferably from about 0.7 or 3.5 mg to about 280 mg or 560 mg/70 kg, more preferably from about 0.5 or 10 mg to about 210 mg/70 kg. The pharmaceutically-acceptable carriers suitable for the preparation of unit dosage forms for peroral administration are well-known in the art. Tablets typically comprise conventional pharmaceutically-compatible adjuvants as: inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of this invention, and can be readily made by a person skilled in the art.

Peroral compositions also include liquid solutions, emulsions, suspensions, and the like. The pharmaceutically-acceptable carriers suitable for preparation of such compositions are well known in the art. Such liquid oral compositions preferably comprise from about 0.012% to about 0.933% of the subject compound, more preferably from about 0.033% to about 0.7%. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. Peroral liquid compositions may also contain one or more components such as sweeteners, flavoring agents and colorants disclosed above.

Other compositions useful for attaining systemic delivery of the subject compounds include sublingual and buccal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

Compositions can also be used to deliver the compound to the site where activity is desired: such as eye drops, gels and creams for ocular disorders.

Compositions of this invention include solutions or emulsions, preferably aqueous solutions or emulsions comprising a safe and effective amount of a subject compound intended for topical intranasal administration. Such compositions preferably comprise from about 0.01% to about 10.0% w/v of a subject compound, more preferably from about 0.1% to about 2.0%. Similar compositions are preferred for systemic delivery of subject compounds by the intranasal route. Compositions intended to deliver the compound systemically by intranasal dosing preferably comprise similar amounts of a subject compound as are determined to be safe and effective by peroral or parenteral administration. Such compositions used for intranasal dosing also typically include safe and effective amounts of: preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetyl cystiene, sodium metabisulfite and others; aromatic agents; viscosity adjustors, such as polymers, including cellulose and derivatives thereof; and polyvinyl alcohol and acids and bases to adjust the pH of these aqueous compositions as needed. The compositions may also comprise local anesthetics or other actives. These compositions can be used as sprays, mists, drops, and the like.

Other preferred compositions of this invention include aqueous solutions, suspensions, and dry powders comprising a safe and effective amount of a subject compound intended for atomization and inhalation administration. Such compositions are typically contained in a container with attached atomizing means. Such compositions also typically include propellants such as chlorofluorocarbons 12/11 and 12/114, and more environmentally friendly fluorocarbons, or other nontoxic volatiles; solvents such as water, glycerol and ethanol, including co-solvents as needed to solvate or suspend the active ingredient; preservatives, such as ascorbic acid or sodium metabisulfite; stabilizers such as cetylpyridinium chloride and benzalkonium chloride; tonicity adjustors such as sodium chloride; buffers; and flavoring agents such as sodium saccharin. Such compositions are useful for treating respiratory disorders, such as asthma and the like.

Other preferred compositions of this invention include aqueous solutions comprising a safe and effective amount of a subject compound intended for topical intraocular administration. Such compositions preferably comprise from about 0.01% to about 0.8% w/v of a subject compound, more preferably from about 0.05% to about 0.3%. Such compositions also typically include: one or more of preservatives, such as benzalkonium chloride or thimerosal; vehicles, such as poloxamers, modified celluloses, povidone and purified water; tonicity adjustors, such as sodium chloride, mannitol and glycerin; buffers such as acetate, citrate, phosphate and borate; and antioxidants such as sodium metabisulfite, butylated hydroxy toluene and acetyl cystiene. Acids and bases can be used to adjust the pH of these formulations as needed.

Other preferred compositions of this invention useful for peroral administration include solids, such as tablets and capsules, and liquids, such as solutions, suspensions and emulsions (preferably in soft gelatin capsules), comprising a safe and effective amount of a subject compound. Such compositions can be coated by conventional methods, typically with pH or time-dependent coatings, such that the subject compound is released in the gastrointestinal tract at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit™ coatings, waxes and shellac.

The compounds of the invention can be administered through, for example, ocular, oral or parenteral routes, including, for example, using formulations suitable as eye drops. For ocular administration, ointments or droppable liquids may be delivered by ocular delivery systems known to the art such as applicators or eye droppers. Such compositions can include mucomimetics such as hyaluronic acid, chondroitin sulfate, hydroxypropyl methylcellulose or polyvinyl alcohol, preservatives such as sorbic acid, EDTA or benzylchromium chloride, and the usual quantities of diluents and/or carriers. See Remington's Pharmaceutical Sciences (16th Ed., Mack Publishing, Easton, Pa., 1980, as well as later editions) for information on pharmaceutical compounding.

Numerous additional administration vehicles will be apparent to those of ordinary skill in the art, including without limitation slow release formulations, liposomal formulations and polymeric matrices.

In another preferred embodiment, the pharmaceutically effective amount is approximately 0.1 or 0.5 to 4 mg/kg body weight daily. Still more preferably, the pharmaceutically effective amount is approximately 1 mg/kg body weight daily. In a preferred embodiment, the amount is administered in once daily doses, each dose being approximately 1 mg/kg body weight.

Compounds of the invention can be used in conjunction with monitoring the improvement (decrease) in the intraocular pressure in a mammal using standard methodology.

The methods of the inventions can be assessed in animal models for ophthalmologic function. For example, improvements in fluid outflow facility can be studied in Rhesus monkeys treated with the compounds and methods of the invention. Aged Rhesus monkeys receive a single transcomeal injection of 30 μL of a test compound (of the invention) at a concentration of about 1 mM in the anterior chamber of one eye, and Barany's solution, as a control, in the adjacent eye. Needle outflow facility is measured under baseline and pilocarpine-stimulated conditions at appropriate time points (for example, 3, 8, 12 and 24 weeks) after the administration of the test compound. Increases in outflow facility in the drug treated vs. the control eye under baseline and cholinergic-stimulated (e.g. pilocarpine) conditions at the various time points are compared. Various routes of administering the cholinergic agent can be studied to determine their influence on outflow facility measured in the experiments. For instance, an intravenous administration versus a direct administration of pilocarpine can be compared. The above experiment demonstrates one method of measuring the improvement in ophthalmologic function.

In addition to measuring increased fluid outflow facility using the methods of the invention, improvements in pilocarpine-stimulated accommodation (i.e, the process of effecting refractive changes in the shape of the lens) can also be assessed in animal studies. As in the regulation of outflow facility, cholinergic input stimulates the movement of the ciliary muscle to control the shape of the lens, and allows accommodation in conditions of low illumination. Accommodation is impaired in a vast majority of individuals and begins to become noticeable to the individual around the age of 40 years. Interestingly, changes in accommodative response occur much earlier in life, around 18 years of age, and progress until vision is noticeably impaired.

Physiological studies on accommodation are conducted following intraocular injection of a test compound and the results are compared relative to the results of control (untreated) animals. In the experiment, primates (for example, Rhesus monkeys) are treated twice a day for four days with 2 μg of prostaglandin $F_2\alpha$ ($PGF_2\alpha$). On days 5–8 both eyes are treated first with 2 μg of $PGF_2\alpha$-followed 2 hours later with an intraocular injection of 10 μL of the test compound at a final concentration of 1 mM. No injection is made to the control eye. 24 Hours after the last injection of the test compound, a course of therapy consisting of once a day dosing for a total of 4 days accommodative responses to i.m. pilocarpine administration is performed following phenylephrine refraction.

Compounds of the invention can be tested to determine corneal penetration to the anterior chamber of the eye following topical administration of eye drops. For example, a test compound is assayed in vitro through an intact rabbit cornea for transcomeal penetration in a standard diffusion chamber apparatus. Corneas are mounted in a chamber at 37° C. with the epithelial side exposed to the test compound in Barany's solution. One mL samples are taken from the endothelial side 1 hour after addition of the test compound at a final concentration of 1 mM to the epithelial chamber. The volume of the chamber is replaced with phosphate buffered saline. The amount of test compound can be measured using any means that can be used to separate the compound and measure its concentration. For example, an HPLC with an attached UV detector can be used to determine the concentration of the test compound that has penetrated the cornea. Penetration values are also determined at later time points, for example, at 5 hours.

Assessment of corneal penetration of compounds of the invention can be determined in vivo, for example, in Cynomolgus monkeys. During these studies, the penetration of a test compound into the eye over a period of 5 hours is evaluated using an eye-cup containing a solution of 10 mM of the test compound in Barany's solution. At the end of the experiment the eye cup is removed, the eye is repeatedly flooded with Barany's solution and a sample of intraocular fluid is removed from the anterior chamber with a needle inserted through the cornea. The quantity of the test compound in the intraocular fluid is determined using, for example, HPLC methods.

The activity of the compounds of the invention in breaking, reversing or inhibiting the formation of AGEs or AGE-mediated crosslinks can be assayed by any of the methods described in U.S. Pat. No. 5,853,703.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

While this invention has been described with an emphasis upon preferred embodiments, it will be obvious to those of ordinary skill in the art that variations in the preferred devices and methods may be used and that it is intended that the invention may be practiced otherwise than as specifically described herein. Accordingly, this invention includes all modifications encompassed within the spirit and scope of the invention as defined by the claims that follow.

What is claimed:

1. A method of decreasing intraocular pressure in an animal, including a human, comprising administering an intraocular pressure decreasing amount of a compound of the formula I:

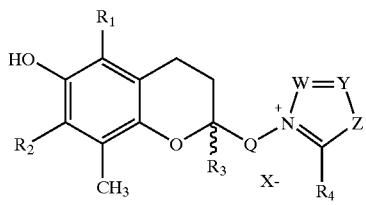

wherein:
a. W and Y are independently N or, respectively, $CR^W$ or $CR^Y$;
b. Z is O, S or $NR^Z$;
c. Q is —$CH_2$— or —(CO)—$CH_2$—, where the methylene is bonded to a ring nitrogen;
d. $R^W$ and $R^Y$ are independently hydrogen, alkyl, —C≡$CR^E$, —$CH_2$—C≡$CR^P$, alkenyl, aryl, arylalkyl, aryloxy, arylthio, amino, alkylamino, arylamino, dialkylamino, diarylamino, $CH_3C(O)NH$—, fluoroalkyl, perfluoroaryl, hydroxyalkyl, $C(O)NH_2$, and $S(O)_2NH_2$ or, together with their ring carbon atoms form a fused 6-membered aromatic or heteroaromatic ring, wherein $R^E$ or $R^P$ is alkyl, hydrogen, hydroxyalkyl or aryl;
e. $R^Z$ is alkyl, —$CH_2$—C≡$CR^P$, aryl, arylalkyl, or aroylalkyl;
f. $R^1$ and $R^2$ are independently hydrogen, alkyl or hydroxymethyl;
g. $R^3$ is hydrogen or methyl;
h. $R^1$ is acetamido, hydrogen, methyl, amino, —C≡$CR^E$, —$CH_2$—C≡$CR^P$ alkylthio, fluoromethyl, difluoromethyl, trifluoromethyl, cyanomethyl, hydroxyalkyl, alkoxycarbonyl-methyl, 1-(alkoxycarbonyl)-1-hydroxyalkyl or aminocarbonylmethyl;
i. Ar, or aryl, refers to a $C_6$ or $C_{10}$ aromatic ring, optionally substituted as set forth below, or a 5- or 6-membered heteroaromatic (heteroaryl) ring containing at least one and up to three atoms of N for the 6-membered heteroaryl ring and from one to three atoms of N or one atom of O or S and zero to two atoms of N for the 5-membered heteroaryl ring; each heteroaromatic ring can be substituted with up to two amino-, dialkylamino-, pyrrolidin-1-yl, piperidin-1-yl, morpholin-4-yl, thiamorpholin-4-yl, 4-(aryl)piperidin-1-yl, 4-(aryl)piperazin-1-yl-(said aryl group optionally substituted as described below), halo (particularly fluoro) or alkylenedioxy groups, or fused to a substituted benzene, pyridine, pyrimidine, pyridazine or triazine ring, and wherein $C_6$ or $C_{10}$ aromatic and heteroaromatic rings can be additionally substituted;
j. $C_6$ or $C_{10}$ aromatic rings can be additionally substituted with acylamino, acyloxyalkyl, alkanoyl, alkanoylalkyl, alkenyl, alkoxy, alkoxycarbonyl, alkoxycarbonylalkyl, alkyl, alkylamino, $(C_1-C_3)$-alkylenedioxy, alkylsulfonyl, alkylthio, allyl, amino, benzoyl, carboxy, carboxyalkyl, cyano, cycloalkyl, dialkylamino, halo, fluoromethyl, difluoromethyl, trifluoromethyl, hydroxy, $(C_1-C_6)$-hydroxyalkyl, mercapto, nitro, phenoxy, phenyl, phenylalkyl, sulfamoyl, sulfo (—$SO_3H$), aminosulfonyl ($H_2NSO_2$—), phenylsulfonyl, or phenylsulfinyl;
k. heteroaromatic rings can be additionally substituted with acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, cyano, dialkylamino, halo, fluoralkyl, hydroxy, mercapto, nitro, phenyl, phenoxy, pyrrolidin-1-yl, piperidin-1-yl, 4-arylpiperidin-1-yl, morpholin-4-yl, 4-arylpiperazin-1-yl, sulfamoyl, fluoromethyl, difluoromethyl, or trifluoromethyl;
l. the halo atoms can be fluoro, chloro, bromo or iodo; and
m. $X^-$ is a pharmaceutically acceptable anion;
and pharmaceutically acceptable acid addition salts of said compounds.

2. The method of claim 1, wherein anion X— is chloride, bromide, mesylate, tosylate, brosylate, mesitylene sulfonate, fumarate, maleate or acetate.

3. The method of claim 1, comprising administering an intraocular pressure decreasing amount of a compound of the formula I,
wherein:
d'. $R^W$ and $R^Y$ are independently hydrogen, alkyl, aryloxy, arylthio, amino, alkylamino, dialkylamino, $CH_3C(O)NH$—, fluoroalkyl, perfluoroaryl, or hydroxyalkyl or, together with their ring carbon atoms form a fused 6-membered aromatic or heteroaromatic ring;
f'. $R^1$ and $R^2$ are methyl;
i'. Ar, or aryl, refers to a $C_6$ or $C_{10}$ aromatic ring, optionally substituted as set forth below, or a 5- or 6-membered heteroaromatic (heteroaryl) ring containing at least one and up to three atoms of N for the 6-membered heteroaryl ring and from one to three atoms of N or one atom of O or S and zero to two atoms of N for the 5-membered heteroaryl ring; each heteroaromatic ring can be substituted with up to two amino-, dialkylamino-, pyrrolidin-1-yl, piperidin-1-yl, morpholin-4-yl, thiamorpholin-4-yl, 4-(aryl)piperidin-1-yl, 4-(aryl)piperazin-1-yl-(said aryl group optionally substituted as described below), halo (particularly fluoro) or fused to a substituted benzene ring, and wherein $C_6$ or $C_{10}$ aromatic and heteroaromatic rings can be additionally substituted;
j'. $C_6$ or $C_{10}$ aromatic rings can be additionally substituted with acylamino, acyloxyalkyl, alkanoyl, alkanoylalkyl, alkenyl, alkoxy, alkoxycarbonyl, alkoxycarbonylalkyl, alkyl, alkylamino, $(C_1-C_3)$-alkylenedioxy, alkylsulfonyl, alkylthio, allyl, amino, benzoyl, carboxy, carboxyalkyl, cycloalkyl, dialkylamino, halo, fluormethyl, difluoromethyl, trifluoromethyl, hydroxy, $(C_2-C_6)$-hydroxyalkyl, mercapto, nitro, phenoxy, phenyl, phenylalkyl, sulfamoyl, sulfo, aminosulfonyl, phenylsulfonyl, or phenylsulfinyl;
k'. heteroaromatic rings can be additionally substituted with acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, dialkylamino, halo, fluoralkyl, hydroxy, mercapto, nitro, phenyl, phenoxy, pyrrolidin-1-yl, piperidin-1-yl, 4-arylpiperidin-1-yl, morpholin-4-yl, 4-arylpiperazin-1-yl, sulfamoyl, fluoromethyl, difluoromethyl or trifluoromethyl; and
l'. the halo atoms can be fluoro, chloro or bromo.

4. The method of claim 3 comprising administering an intraocular pressure decreasing amount of a compound of the formula I,
wherein:
a'. W and Y are $CR^W$ and $CR^Y$, respectively;
b'. Z is S, and the compounds are thiazolium salts; and h'. $R^4$ is acetamido, hydrogen, methyl, amino, alkylthio, fluoromethyl, difluoromethyl or trifluoromethyl.

5. The method of claim 3 comprising administering an intraocular pressure decreasing amount of a compound of the formula I, wherein:
 a'. W is N and Y is $CR^Y$;
 b'. Z is S, and the compounds are [1,3,4]-thiadiazolium salts;
 d". $R^Y$ is hydrogen, alkyl, aryloxy, arylthio, amino, alkylamino, dialkylamino, fluoroalkyl, perfluoroaryl, or hydroxyalkyl; and
 h'. $R^4$ is acetamido, hydrogen, methyl, amino, alkylthio, fluoromethyl, difluoromethyl or trifluoromethyl.

6. The method of claim 3 comprising administering an intraocular pressure decreasing amount of a compound of the formula I, wherein:
 h'. $R^4$ is hydrogen, methyl, amino, alkylthio, fluoromethyl or difluoromethyl.

7. The method of claim 6 comprising administering an intraocular pressure decreasing amount of a compound of the formula I, wherein Q=—(CO)—$CH_2$—.

8. The method of claim 7 comprising administering an intraocular pressure decreasing amount of a compound of the formula I, wherein:
 a'. W is N and Y is $CR^Y$; and
 b'. Z is O and the compounds are [1,3,4]-oxadiazolium salts; and
 d". $R^Y$ is hydrogen, alkyl, aryloxy, arylthio, amino, alkylamino, dialkylamino, fluoroalkyl, perfluoroaryl, or hydroxyalkyl.

9. The method of claim 7 comprising administering an intraocular pressure decreasing amount of a compound of the formula I, wherein:
 a'. W is N and Y is $CR^Y$;
 b'. Z is $NR^Z$ and the compounds are [1,2,4]-triazolium salts; and
 d". $R^Y$ is hydrogen, alkyl, aryloxy, arylthio, amino, alkylamino, dialkylamino, fluoroalkyl, perfluoroaryl, or hydroxyalkyl.

10. The method of claim 7 comprising administering an intraocular pressure decreasing amount of a compound of the formula I, wherein:
 a'. W and Y are $CR^W$ and $CR^Y$, respectively; and
 b'. Z is $NR^Z$, and the compounds are imidazolium salts.

11. The method of claim 7 comprising administering an intraocular pressure decreasing amount of a compound of the formula I, wherein:
 a'. W is $CR^W$ and Y is N;
 b'. Z is S and the compounds are [1,2,4]-thiadiazolium salts; and
 d". $R^W$ is hydrogen, alkyl, aryloxy, arylthio, amino, alkylamino, dialkylamino, fluoroalkyl, perfluoroaryl, or hydroxyalkyl.

12. The method of claim 6 comprising administering an intraocular pressure decreasing amount of a compound of the formula I, wherein Q=—$CH_2$—.

13. The method of claim 12 comprising administering an intraocular pressure decreasing amount of a compound of the formula I, wherein:
 a'. W is N and Y is C;
 b'. Z is O and the compounds are [1,3,4]-oxadiazolium salts; and
 d". $R^Y$ is hydrogen, alkyl, aryloxy, arylthio, amino, alkylamino, dialkylamino, fluoroalkyl, perfluoroaryl, or hydroxyalkyl.

14. The method of claim 12 comprising administering an intraocular pressure decreasing amount of a compound of the formula I, Q=—$CH_2$—wherein:
 a'. W is N and Y is $CR^Y$;
 b'. Z is $NR^Z$ and the compounds are [1,2,4]-triazolium salts; and
 d". $R^Y$ is hydrogen, alkyl, aryloxy, arylthio, amino, alkylamino, dialkylamino, fluoroalkyl, perfluoroaryl, or hydroxyalkyl.

15. The method of claim 12 comprising administering an intraocular pressure decreasing amount of a compound of the formula I, Q=—$CH_2$—wherein:
 a'. W and Y are $CR^W$ and $CR^Y$, respectively; and
 b'. Z is $NR^Z$, and the compounds are imidazolium salts.

16. The method of claim 12 comprising administering an intraocular pressure decreasing amount of a compound of the formula I, wherein:
 a'. W is $CR^W$ and Y is N;
 b'. Z is S and the compounds are [1,2,4]-thiadiazolium salts; and
 d". $R^W$ is hydrogen, alkyl, aryloxy, arylthio, amino, alkylamino, dialkylamino, fluoroalkyl, perfluoroaryl, or hydroxyalkyl.

17. The method of claim 1, wherein the administered compound is of formula I, wherein Q=—(CO)—$CH_2$— and:
 1. W and Y are $C(CH_3)$;
 2. Z is S;
 3. $R_1$=R2=R3=$CH_3$ or $R_1$=$R_3$=$CH_3$, $R_2$=H; and
 4. $R_4$ is H or $CH_3$.

18. The method of claim 1, wherein the administered compound is of formula I, wherein Q=—(CO)—$CH_2$— and:
 1. W is N, Y is $C(CH_3)$;
 2. Z is S;
 3. $R_1$=$R_2$=$R_3$=$CH_3$ or $R_1$=$R_3$=$CH_3$, $R_2$=H; and
 4. $R_4$ is H or $CH_3$.

19. The method of claim 1, wherein the administered compound is of formula I, wherein Q=—(CO)—$CH_2$— and:
 1. W is N and Y is $C(CH_3)$;
 2. Z is N—$C_6H_5$;
 3. $R_1$=$R_3$=$CH_3$, $R_2$=H or R=$R_2$=$R_3$=$CH_3$;
 4. $R_4$ is H.

20. The method of claim 1, wherein the administered compound is of formula I, wherein Q=—(CO)—$CH_2$— and:
 1. W is N and Y is $C(CH_3)$;
 2. Z is N—$CH_3$;
 3. $R_1$=$R_2$=$CH_3$, $R_3$=H;
 4. $R_4$ is H.

21. The method of claim 1, wherein the administered compound is of formula I, wherein Q=—$CH_2$— and:
 1. W and Y are $C(CH_3)$;
 2. Z is S;
 3. $R_1$=$R_2$=$R_3$=$CH_3$ or $R_1$=$R_3$=$CH_3$, $R_2$=H; and
 4. $R_4$ is H or $CH_3$.

22. The method of claim 1, wherein the administered compound is of formula I, Q=—$CH_2$— and:
 1. W is N, Y is $C(CH_3)$;
 2. Z is S;
 3. $R_1$=$R_2$=$R_3$=$CH_3$ or $R_1$=$R_3$=$CH_3$, $R_2$=H; and
 4. $R_4$ is H or $CH_3$.

23. The method of claim 1, wherein the administered compound is of formula I, wherein Q=—$CH_2$— and:

1. W is N and Y is C(CH$_3$);
2. Z is N-C$_6$H$_5$;
3. R$_1$=R$_2$=R$_3$=CH$_3$ or R$_1$=R$_3$=CH$_3$, R$_2$=H;
4. R$_4$ is H.

24. A compound of the formula I:

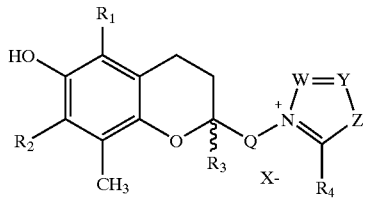

wherein:
a. W and Y are independently N or, respectively, CR$^W$ or CR$^Y$;
b. Z is O, S or NR$^Z$;
c. Q is —CH$_2$— or —(CO)—CH$_2$—, where the methylene is bonded to a ring nitrogen;
d. R$^W$ and R$^Y$ are independently hydrogen, alkyl, —C≡CR$^E$, —CH$_2$—C≡CR$^P$, alkenyl, aryl, arylalkyl, aryloxy, arylthio, amino, alkylamino, arylamino, dialkylamino, diarylamino, CH$_3$C(O)NH—, fluoroalkyl, perfluoroaryl, hydroxyalkyl, C(O)NH$_2$, and S(O)$_2$NH$_2$ or, together with their ring carbon atoms form a fused 6-membered aromatic or heteroaromatic ring, wherein R$^E$ or R$^P$ is alkyl, hydrogen, hydroxyalkyl or aryl;
e. R$^Z$ is alkyl, —CH$_2$—C≡CR$^P$, aryl, arylalkyl, or aroylalkyl;
f. R$^1$ and R$^2$ are independently hydrogen, alkyl or hydroxymethyl;
g. R$^3$ is hydrogen or methyl;
h. R$^4$ is acetamido, hydrogen, methyl, amino, —C≡CR$^E$, —CH$_2$—C≡CR$^P$ alkylthio, fluoromethyl, difluoromethyl, trifluoromethyl, cyanomethyl, hydroxyalkyl, alkoxycarbonyl-methyl, 1-(alkoxycarbonyl)-1-hydroxyalkyl or aminocarbonylmethyl;
i. Ar, or aryl, refers to a C$_6$ or C$_{10}$ aromatic ring, optionally substituted as set forth below, or a 5- or 6-membered heteroaromatic (heteroaryl) ring containing at least one and up to three atoms of N for the 6-membered heteroaryl ring and from one to three atoms of N or one atom of O or S and zero to two atoms of N for the 5-membered heteroaryl ring; each heteroaromatic ring can be substituted with up to two amino-, dialkylamino-, pyrrolidin-1-yl, piperidin-1-yl, morpholin-4-yl, thiamorpholin-4-yl, 4-(aryl)piperidin-1-yl, 4-(aryl)piperazin-1-yl-(said aryl group optionally substituted as described below), halo (particularly fluoro) or alkylenedioxy groups, or fused to a substituted benzene, pyridine, pyrimidine, pyridazine or triazine ring, and wherein C$_6$ or C$_{10}$ aromatic and heteroaromatic rings can be additionally substituted as set forth below;
j. C$_6$ or C$_{10}$ aromatic rings can be additionally substituted with acylamino, acyloxyalkyl, alkanoyl, alkanoylalkyl, alkenyl, alkoxy, alkoxycarbonyl, alkoxycarbonylalkyl, alkyl, alkylamino, (C$_1$-C$_3$)-alkylenedioxy, alkylsulfonyl, alkylthio, allyl, amino, benzoyl, carboxy, carboxyalkyl, cyano, cycloalkyl, dialkylamino, halo, fluoromethyl, difluoromethyl, trifluoromethyl, hydroxy, (C$_1$-C$_6$)-hydroxyalkyl, mercapto, nitro, phenoxy, phenyl, phenylalkyl, sulfamoyl, sulfo (—SO$_3$H), aminosulfonyl (H$_2$NSO$_2$—), phenylsulfonyl, or phenylsulfinyl;
k. heteroaromatic rings can be additionally substituted with acylamino, alkanoyl, alkoxy, alkoxycarbonyl, alkoxycarbonylalkyl, alkyl, alkylamino, alkylsulfonyl, alkylthio, amino, arylsulfonyl, aryl sulfonyl, benzoyl, carboxy, cyano, dialkylamino, halo, fluoralkyl, hydroxy, mercapto, nitro, phenyl, phenoxy, pyrrolidin-1-yl, piperidin-1-yl, 4-arylpiperidin-1-yl, morpholin-4-yl, 4-arylpiperazin-1-yl, sulfamoyl, fluoromethyl, difluoromethyl, or trifluoromethyl;
l. the halo atoms can be fluoro, chloro, bromo or iodo; and
m. X$^-$ is a pharmaceutically acceptable anion;
and pharmaceutically acceptable acid addition salts of said compounds.

* * * * *